United States Patent [19]
Schade et al.

[11] Patent Number: 4,755,609
[45] Date of Patent: Jul. 5, 1988

[54] PROCESS FOR THE PREPARATION OF THIOCYANATOMETHYLTHIOBENZOTHIAZOLES

[75] Inventors: Gerold Schade; Karlfried Wedemeyer, both of Cologne; Herbert Diehl, Leverskusen, all of Fed. Rep. of Germany

[73] Assignee: Bayer Aktiengesellschaft, Leverkusen, Fed. Rep. of Germany

[21] Appl. No.: 828,929

[22] Filed: Feb. 12, 1986

[30] Foreign Application Priority Data

Feb. 13, 1985 [DE] Fed. Rep. of Germany ....... 3504966

[51] Int. Cl.$^4$ .......................................... C07D 277/82
[52] U.S. Cl. .................................................... 548/169
[58] Field of Search ........................... 548/169; 508/56

[56] References Cited

U.S. PATENT DOCUMENTS

| 3,006,965 | 10/1961 | Schrader | 568/56 |
| 3,463,785 | 8/1969 | Buckman et al. | 548/169 |
| 3,520,976 | 7/1970 | Buckman et al. | 514/367 |
| 3,669,981 | 6/1972 | Pera et al. | 548/173 |
| 3,992,432 | 11/1976 | Napier et al. | 260/684 |
| 4,014,891 | 3/1977 | Goralski et al. | 568/56 |

FOREIGN PATENT DOCUMENTS 1670221 7/1970 Fed. Rep. of Germany .
1768050 7/1971 Fed. Rep. of Germany .

OTHER PUBLICATIONS

Justus Liebigs, Annalen Chem. 563, 54 (1949).
English Translation of Japanese Kokai Patent Publication No. 60-132971, published Jul. 16, 1985.
Weber et al, Phase Transfer Catalysis in Organic Synthesis (1977), Springer-Verlag, N.Y.
Dilworth et al, Tetrahedron vol. 42, No. 14, pp. 3731, 3739-3741, 3751.
W. Reeves et al, Chem. Abstracts 86:71816g (1977).
G. Szabo et al, Chem. Abstracts 97:169893g (1982).
J. Harris et al, J. Org. Chem., 1982, 47, 4789-4791.

Primary Examiner—Mary E. Ceperley
Attorney, Agent, or Firm—Sprung Horn Kramer & Woods

[57] ABSTRACT

The present invention relates to the preparation of thiocyanatomethylthiobenzothiazoles by the reaction of halomethylthiobenzothiazoles with thiocyanates at elevated temperature in aqueous solution in the presence of a phase transfer catalyst.

6 Claims, No Drawings

PROCESS FOR THE PREPARATION OF THIOCYANATOMETHYLTHIOBENZOTHIAZOLES

The present invention relates to a process for the preparation of thiocyanatomethylthiobenzothiazoles by reaction of halomethylthiobenzothiazoles with thiocyanates.

Thiocyanatomethylthiobenzothiazoles, while find application, for example, as microbiocides, are prepared according to U.S. Pat. No. 3,520,976 by reaction of chloromethylthiobenzothiazoles with metal rhodanide (thiocyanate) in the presence of organic solvents.

Disadvantageous in this process is the presence of an organic solvent, which entails a number of difficulties on transfer to the industrial scale.

Thus, for example, the organic solvent must be evaporated off to obtain the product, in which process problems may arise due to the fact that the metal chlorides formed during the reaction crystallize out at the heat-transferring surfaces. The encrustations so produced impede the heat transfer very considerably.

After the evaporation of the solvent, the product must be subjected to costly washing and drying operations for the removal of salts, in which process it is again diluted with a solvent which must subsequently be removed.

The recovery and purification of the organic solvent used is necessary for ecological reasons. This requires, however, additional technical expense, which likewise takes place at the expense of the economicalness of the process.

There has now been found a process for the preparation of thiocyanatomethylthiobenzothiazoles of the formula

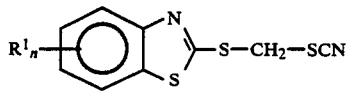
(I)

wherein
$R^1$ represents hydrogen, halogen, a nitro, amino, hydroxy or an alkyl group and
n represents 1 or 2,
which is characterised in that halomethylthiobenzothiazoles of the formula

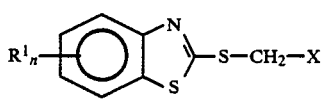
(II)

wherein
$R^1$ and n have the above-named meaning and
X represents halogen,
are reacted with thiocyanates of the formula

  $M^\oplus SCN^\ominus$ (III)

wherein
M represents an alkali metal ion or an ammonium ion, at elevated temperature in aqueous solution in the presence of a phase transfer catalyst.

As halogens there may be mentioned: fluorine, chlorine, bromine and iodine, preferably fluorine, chlorine and bromine, particularly preferably chlorine;

As alkyl groups those with 1 to 12 carbon atoms, preferably 1 to 5 carbon atoms, such as methyl, ethyl, n-propyl, isopropyl, n-butyl, isobutyl, tert.-butyl, pentyl, hexyl, heptyl, octyl, nonyl, decyl, undecyl and dodecyl, preferably methyl, ethyl, n-propyl, isopropyl, n-butyl, isobutyl, tert.-butyl and pentyl.

The thiocyanatomethylthiobenzothiazole of the formula (IV)

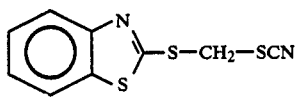
(IV)

is prepared particularly preferably by the process according to the invention.

To carry out the process according to the invention, the halomethylthiobenzothiazoles of the formula (II), in particular the corresponding 2-chloromethylthiobenzothiazoles, are reacted with aqueous thiocyanate solution at elevated temperature in the presence of a phase transfer catalyst. As phase transfer catalysts it is possible to use, for example:

(a) Quaternary onium salts of the general formula

 $AR^2R^3R^4R^{5\oplus} X^\ominus$ wherein $R^2$ to $R^5$, independently of one another, represent alkyl, aryl or aralkyl with 1 to 20 carbon atoms, A represents nitrogen or phosphorus and X represents halogen, such as fluorine, chlorine, bromine or iodine, preferably chlorine or bromine, hydrogen sulfate or thiocyanate. The following quaternary onium salts may be mentioned by way of example: triethylbenzylammonium chloride, tetrabutylammonium bromide, -fluoride and -hydrogensulfate, tricaprylylmethylammonium chloride, hexadecyltrimethylammonium bromide, benzyldimethyldodecylammonium iodide, tetrabutylphosphonium chloride and hexadecyltriphenylphosphonium bromide.

In the case that A in the above formula represents nitrogen, several of the radicals $R^2$ to $R^5$ may together form a ring with 4 to 6C atoms. This is the case, for example, with cetylpyridinium chloride.

(b) Crown ethers such as 15-crown-5, 18-crown-6 and dibenzo-18-crown-6.

(c) Polyethers of the general formula

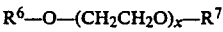 $R^6-O-(CH_2CH_2O)_x-R^7$ wherein $R^6$ and $R^7$, independently of one another, represent hydrogen, alkyl or optionally substituted aryl, with 1 to 20, preferably 1 to 12 carbon atoms, and x represents an integer from 4 to 40.

As examples there may be mentioned: polyethylene glycol, polyethylene glycol monoethyl ether, polyethylene glycol dimethyl ether, ethoxylated dodecyl alcohol, ethoxylated phenol and/or ethoxylated isononylphenol. The polyethers named here are often mixtures of homologues in which x covers a certain range.

The present process according to the invention is not limited to the above-named possible phase transfer catalysts which represent only a selection (cf. other literature on phase transfer catalysts, e.g. Dehmlow and Dehmlow, Phase Transfer Catalysis, Weinheim 1983).

In principle, all catalysts which are capable of transferring thiocyanate ions in adequate concentration to the organic phase are suitable for the process according to the invention.

In general, the phase transfer catalysts in the process according to the invention are used in quantities of about 0.001 to 0.1, preferably 0.002 to 0.01 mol per mol of halomethylthiobenzothiazole used. They may be used both individually and in mixtures with each other.

As thiocyanates, the alkali metal and/or ammonium thiocyanates, preferably sodium thiocyanate, may be used. Their concentration in the aqueous solution is not critical and may lie in the range between 20% by weight and saturation; preferably the concentration of the thiocyanate in the aqueous solution lies at 30 to 60% by weight.

According to the process according to the invention, the thiocyanates of the formula (III) are used in at least stoichiometric quantities, referred to the halomethylthiobenzothiazoles to be used. An excess of up to 50% by weight of thiocyanate may often be expedient. Normally about 1.0 to 1.2 mol of thiocyanate of the formula (III) per mol of halomethylthiobenzothiazole of the formula (II) is used in the process according to the invention.

The process according to the invention is in general carried out at temperatures of about 70° to 110° C., preferably 75° to 90° C. If the work is done in a closed vessel, the reaction can also be carried out under overpressure at temperatures of up to 120° C. At these temperatures 2-chloromethylthiobenzothiazole, for example, is liquid so that an intensive mixing of the heterogeneous mass is possible.

The duration of the reaction depends on the type and on the quantity of the catalyst used and the reaction temperature, and in general amounts to several hours. The end of the reaction is expediently detected analytically, e.g. by gas or thin-layer chromatography.

Without the addition of phase transfer catalysts, no technically usable reaction velocities are achieved.

After the reaction is complete, the working up takes place in a simple manner, for example by separation of the liquid thiocyanatomethylthiobenzothiazole from the aqueous common salt solution.

Although the acceleration of substitution reactions in heterogeneous reaction mixtures by the addition of phase transfer catalysts constitutes a method known per se also for the preparation of organic thiocyanates (cf. DE-OS (German Published Specification No.) 1,768,050) it was nevertheless not to be anticipated that, for example, thiocyanatomethylthiobenzothiazole can also be prepared in this way in a smooth reaction. It is, after all, known from Liebigs Annalen Chem. 563, 54 (1949) that chloromethylsulphides easily hydrolyze. Thus it is stated in the second paragraph on page 57 of the named literature source that "The α-halogenated thioethers very easily decompose on contact with water". The hydrolysis thus proceeds according to the following formula scheme $$2R-S-CH_2-Cl + H_2O \rightarrow R-S-CH_2-S-R + HCHO + 2HCl.$$

Because of the known sensitivity to hydrolysis of the α-halogenated thioethers it was improbable that a phase transfer reaction with aqueous thiocyanate solution would yield, for example, thiocyanatomethylthiobenzothiazole with good yield and purity. This applies in particular in view of the reaction conditions which are actually necessary for an industrially usable reaction velocity. A high purity of the product formed was, however, indispensable since thiocyanatomethylthiobenzothiazole can hardly be purified later because of its special properties (cf. DE-OS (German Published Specification No.) 1,670,221).

It was therefore all the more surprising that the thiocyanatomethylthiobenzothiazoles were obtained by the process according to the invention with very good yield and with high purities.

The process according to the invention will be explained by the following examples, without, however, it being limited to these examples.

EXAMPLE 1

204.5 g of 96% chloromethylthiobenzothiazole are suspended in 200 ml of water and 90 g of sodium rhodanide (thiocyanate) as well as 2.3 g of benzyltriethylammonium chloride are added. The mixture is stirred for 10 h at 80° C. After cooling, the precipitated oily product is separated off.

Yield 226 g, content 82%, conversion 97%.

EXAMPLE 2

If the procedure is as in Example 1, but at 90° C., complete conversion is achieved after 7 h.

EXAMPLE 3

If the procedure is as in Example 1, but with approx. 1 mol % of tetrabutylammonium bromide as catalyst, complete conversion is achieved after 16 h.

EXAMPLE 4

If the procedure is as in Example 1, but with approx. 1 mol % of 18-crown-6 as catalyst, 94% conversion is achieved after 12 h.

EXAMPLE 5

If the procedure is as in Example 4, but with approx. 5 mol % (referred to the structural unit $(CH_2CH_2O)_6$)) of polyethylene glycol (average molecular weight 1550) as catalyst, 96% conversion is achieved after 12 h.

EXAMPLE 6

If the procedure is as in Example 5, but with the same quantity by weight of 4-isononylphenol-10-glycol ether (NP 10) as catalyst, 90% conversion is achieved after 9.5 h.

EXAMPLE 7

If the procedure is as in Example 1, but in a closed vessel at 110° C., complete conversion is achieved after 5 h.

EXAMPLE 8

(Comparative Example)

If the procedure is as in Example 1, but without catalyst, with 41% conversion is achieved after 10 h, only 57% after 20 h and only 68% conversion after 30 h.

What is claimed is:

1. A process for the preparation of a thiocyanatomethylthiobenzothiazole of the formula

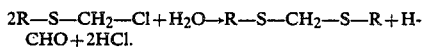

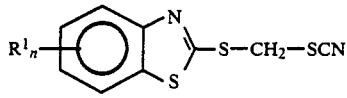

wherein
- R$^1$ represents hydrogen, halogen, a nitro, amino hydroxyl or an alkyl group and
- n represents 1 or 2, wherein a halomethylthiobenzothiazole of the formula

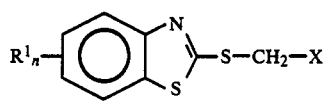

wherein
- R$^1$ and n have the above-named meaning and
- X represents halogen, is reacted with a thiocyanate of the formula

wherein
- M represents an alkali metal or ammonium at elevated temperature in aqueous solution in the presence of a phase transfer catalyst selected from quaternary onium salts, crown ethers and polyethers, wherein the reaction is carried out at a temperature of 70° to 110° C.

2. A process according to claim 1, wherein the phase transfer catalyst is used in quantities of 0.001 to 0.1 mol per mol of halomethylthiobenzothiazole.

3. A process according to claim 1 wherein the phase transfer catalyst is a quaternary onium salt of the formula

wherein R$^2$ to R$^5$, independently of one another, represent alkyl, aryl or aralkyl with 1 to 20 carbon atoms, A represents nitrogen or phosphorus and X represents halogen, hydrogen sulfate or thiocyanate and in the case that A in the above formula represents nitrogen, two of the radicals R$^2$ to R$^5$ may together form a pyridinium ring.

4. A process according to claim 1 wherein the phase transfer catalyst is a polyether of the formula

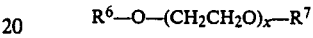

wherein R$^6$ and R$^7$, independently of one another, represent hydrogen, alkyl or optionally substituted aryl, with 1 to 20 carbon atoms, and x represents an integer from 4 to 40.

5. A process according to claim 1 wherein the phase transfer catalyst is a crown ether selected from 15-crown-5, 18-crown-6 and dibenzo-18-crown-6.

6. A process according to claim 4 wherein the alkyl or optionally substituted aryl defined by R$^6$ and R$^7$ of the polyether have 1 to 12 carbon atoms.

* * * * *